United States Patent
Cavallo et al.

(12)

(10) Patent No.: US 6,486,139 B1
(45) Date of Patent: Nov. 26, 2002

(54) OPHTHALMIC SOLUTION COMPRISING GLYCOGEN

(75) Inventors: Giovanni Cavallo, Ostia; Alberto Campana, Rome; Leonardo Marchitto, Cupra Marittima; Mario Pinza, Corsico, all of (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 09/623,502

(22) PCT Filed: Mar. 11, 1999

(86) PCT No.: PCT/EP99/01624

§ 371 (c)(1),
(2), (4) Date: Sep. 19, 2000

(87) PCT Pub. No.: WO99/47120

PCT Pub. Date: Sep. 23, 1999

(30) Foreign Application Priority Data

Mar. 19, 1998 (IT) .......................... MI98A0555

(51) Int. Cl.$^7$ ............................................ A61K 31/715
(52) U.S. Cl. ........................................ 514/54; 514/912
(58) Field of Search .................................... 514/54, 912

(56) References Cited

U.S. PATENT DOCUMENTS 4,039,662 A * 8/1977 Hecht et al. .................. 514/54

* cited by examiner

Primary Examiner—Zohreh Fay
(74) Attorney, Agent, or Firm—Oblon, Spivak, McClelland, Maier & Neustadt, P.C.

(57) ABSTRACT

The present invention relates to humectant and lubricant solution for ophthalmic use based on a glycogen polysaccharide.

14 Claims, No Drawings

OPHTHALMIC SOLUTION COMPRISING GLYCOGEN

This invention relates to a humectant and lubricant solution for ophthalmic use based on a glycogen polysaccharide.

It is known that the instillation of humectant and lubricant solutions into the eye is indicated in some circumstances. These solutions are all the more useful if they mimic the functions of natural tear fluid.

This type of humectant and lubricant solution has therefore been given the name of "artificial tears", even when the capacity to mimic natural tear fluid is not entirely satisfactory.

Artificial tears are used, for example, to alleviate the symptoms of dry keratoconjunctivitis, exposure-induced keratopathies and other situations resulting in dry eye syndrome. In addition to this artificial tears are useful to wearers of contact lenses, particularly in the case of hard lenses.

One of the properties required from artificial tears is that they should produce a sensation of well-being and freshness which lasts for a sufficient length of time.

In the past it was considered that in order to achieve this objective artificial tears should have a high viscosity, and this was achieved by adding polymers such as cellulose esters, polyethylene glycol, polystyrene sulphonate or polyvinyl acid.

However, such artificial tears do not satisfactorily mimic the properties of natural tear fluid which, as is known, has a rather low viscosity (between 1 and 6 cP) [J. M. Tiffany, "International Ophthalmology", 15, 371–376, 1991 H. Botner, T. Waaler and O. Wik, "Drug Development and Industrial Pharmacy", 16(5), 755–768, 1990].

In addition to this it has been shown that a viscosity greater than 20 cP is generally regarded as being uncomfortable on account of eyelid movement (J. I. Greaves, O. Olejnik and C. G. Wilson, "Pharma. Sciences", 2(1 13–33, 1992). Also, viscosities in excess of 40–50 cP can cause occlusion of the tear duct and give the patient a continual sensation of having a foreign body in the eye (M. Amorosa, "Principi di Tecnica Farmaceutica", (Principles of pharmaceutical technology), 399, 1983).

U.S. Pat. No. 4,039,662 proposes that this disadvantage should be overcome through a low viscosity ophthalmic solution containing dextran or arabinogalactan together with benzylalkonium chloride. In particular, the abovementioned patent specifies that the polysaccharide component alone without benzylalkonium chloride is incapable of remaining adsorbed onto the cornea for a sufficiently long period (column 3, lines 9–13). In explanation of this behaviour it is hypothesised that the polysaccharide particles described in the aforesaid patent combine in solution with the benzylalkonium chloride by electrostatic attraction. This seems to form a complex having an electron charge which causes the macromolecule to be adsorbed onto the surface of the cornea (column 3, lines 19–37).

Furthermore, it is known from the literature that aqueous solutions of dextran have an osmotic pressure which is much greater than that of natural tears (F. J. Holly and E. D. Esquivel "Colloid Osmotic Pressure of Artificial Tears", Journal of Ocular Pharmacology, 1, 327–336, 1985). Despite the fact that this contrasts with the principle according to which tho physical proportions of artificial tears should be as similar as possible to those of natural tears, Holly et al. specifically attribute the greater acceptance of dextran-based artificial tears by patients to the said greater oncotic pressure.

Now it has been surprisingly found that glycogen polysaccharides provide an ophthalmic solution of low viscosity and low oncotic pressure and exert a pleasing refreshing, lubricating and humectant effect on the cornea even in the absence of benzylalkonium chloride (Table I).

Therefore, it is an object of this invention to provide the use of a glycogen polysaccharide, as an active ingredient, substantially free of nitrogen when determined by the Kjeldahl method, for the manufacture of ophthalmic sterile aqueous solution useful as an artificial tear.

Preferably the glycogen polysaccharide Is prepared according to patent EP-B-0 654 048.

It has also been found that, in addition to being characterized by a long residence time In the eye, aqueous solutions of glycogen polysaccharides can be filtered to 0.2 microns, and can thus provide sterile solutions up to a concentration of 12% (w/v). In addition to this, these solutions have a low viscosity and a low oncotic pressure.

Typically the quantity of glycogen polysaccharide in the ophthalmic solution according to this invention is of from 0.1 to 12% (w/v).

Preferably it is of from 1 to 6% (w/v). Even more preferably it is of from 2 to 4% (w/v).

Typically the ophthalmic solution according to this invention has a viscosity of between 1 and 9 cP. Preferably it has a viscosity between 2 and 7 cP. Even more preferably, it has a viscosity between 2 and 6 cP.

Typically, the ophthalmic solution according to this Invention has an oncotic pressure of less than 5 mmHg. Preferably it has an oncotic pressure of less than 3 mmHg.

The ophthalmic solution according to this Invention may also contain other conventional ingredients such as: antioxidants, buffers, compounds to render the solution isotonic with tear fluid, stabilising agents, colouring agents and the like.

Typical examples of antioxidants are cysteine, ascorbic acid and taurine. The latter is also particularly preferred on account of its anti-free radical properties.

The quantity of antioxidant in the ophthalmic solution according to this invention will vary widely according to the preselected composition. In the specific case of taurine, the quantity is preferably of from 0.1 to 0.6% (w/v) and, even more preferably, from 0.2 to 0.4% (w/v).

Typical examples of buffers are borate, bicarbonate, acetate and phosphate buffers, and their quantities will be selected so as to regulate the pH of the ophthalmic solution according to this invention between 5 and 8. Preferably the buffer will be a phosphate buffer and the pH of the ophthalmic solution according to the invention will be adjusted between 6.5 and 7.5.

Typical examples of compounds suitable for ensuring that the ophthalmic solution according to this invention is isotonic with natural tear fluid are glycerine, sodium chloride and mannitol.

The quantities of these in the ophthalmic solution according to this invention will vary widely according to the preselected composition. In the particular case of mannitol, the quantity is preferably of from 0.5 to 3% (w/v). Even more preferably it is of from 1.5% to 2% (w/v).

The composition according to this invention may also contain one or more preservatives selected from the group comprising benzylalkonium chloride, thimerosal, methyl parabenes, ethyl parabenes, propyl parabenes and butyl parabenes.

The glycogen polysaccharide used in the examples below was extracted from *Mytilus edulis* or *Mytilus gallus* provincialis using the method described in EP-B-0 654 048 and had the following characteristics:

C: 44.44%

N: absent[1]

reducing sugars[2]: absent $[\alpha]_D^{20}$: 198±1.0 (c=1, water)

mean surface tension[3]:

3% aqueous solution at 25° C.: 66.29 mN/m

6% aqueous solution at 25° C.: 61.04 mN/m

3% aqueous solution at 37° C.: 59.19 mN/m

6% aqueous solution at 7° C.: 58.20 mN/m contact angle with glass[4] at ambient temperature (the comparison test with water yielded a result of 42°):

3% aqueous solution: 32°

6% aqueous solution: 18°.

Notes:

[1] determined by the Kjeldahl method,

[2] determined in accordance with F. D. Snell and Snell, "Colorimetric Method of Analysis" N.Y., 1954, Vol. III, pag. 204,

[3] determined using a Lauda tensiometer,

[4] determined using a contact angle measuring device of the Face Contact Angle Meter, Kyowa Kaimenkagaki Co. Ltd., Nordtest type.

The following examples are intended to illustrate this invention without limiting it in any way.

EXAMPLE 1

Preparation of an Ophthalmic Solution Containing a Glycogen Polysaccharide (Solution A)

| Components | Quantity (g) |
| --- | --- |
| glycogen polysaccharide | 3 |
| D-mannitol | 1.8 |
| taurine | 0.3 |
| monobasic sodium phosphate H$_2$O | 0.2 |
| dibasic sodium phosphate 12 H$_2$O | 1.5 |
| distilled water q.s.p. | 100 ml |

The abovementioned ophthalmic solution was prepared by dissolving the abovementioned components in the prescribed quantity of water at 18–25° C. The product was then filtered using a 0.22 μm filter to sterilise the preparation.

The solution prepared in this way (Solution A) was subdivided into 0.4 ml doses in single-use phials having a capacity of 1 ml. The solution prepared in this way had the following properties:

| | |
| --- | --- |
| pH | 7.18 |
| osmolarity[5] | 272 |
| density[6] (g/ml) at 25° C. | 1.024 |
| density[6] (g/ml) at 37° C. | 1.016 |
| viscosity[7] (cP) | 5 |
| oncotic pressure[8] (mmHg) | 1.7 |
| sterility | sterile |
| mean surface tension[3] (m/Nm) | |
| at 25° C. | 61.80 |
| at 37° C. | 61.90 |

Notes:

[5] determined using the Knauer Automatic Osmometer apparatus,

[6] determined using the Ken Da-310 M Mettler - Toledo densimeter,

[7] determined using a Mettler Rheomat Rm-180 rheometer,

[8] determined using the Osmomat 050 Colloid Osmometer apparatus from the Gonotec company, Under the same conditions the oncotic pressure of a 3% w/w solution of dextran was 16.4 mmHg.

EXAMPLE 2

Preparation of Solution B

Working in a manner similar to that described in Example 1 above, a second solution was prepared and comprised:

| Components | Quantity (g) |
| --- | --- |
| glycogen polysaccharide | 3 |
| mannitol | 1.8 |
| sodium chloride | 0.070 |
| phosphate buffer | pH 7, 1–7.4 |
| distilled water q.s.p. | 100 ml |

The solution prepared in this way had the following characteristics:

| | |
| --- | --- |
| sterility | sterile |
| oncotic pressure[8] (mmHg) | 1.7 |
| mean surface tension[3] m/Nm | |
| at 25° C. | 61.43 |
| at 37° C. | 60.02 |

Notes:

[3] determined as in note[3] above.

[8] determined as in note[8] above.

EXAMPLE 3

Preparation of an Ophthalmic Solution Containing a Glycogen Polysaccharide (Solution C)

Operating in a manner similar to that described in Example 1 above a third solution was prepared and comprised:

| Components | Quantity (g) |
| --- | --- |
| glycogen polysaccharide | 3 |
| D-mannitol | 1.8 |
| taurine | 0.3 |
| monobasic sodium phosphate H$_2$O | 0.2 |
| dibasic sodium phosphate 12 H$_2$O | 1.5 |
| distilled water q.s.p. | 50 ml |

The solution prepared in this way (Solution C) had the following characteristcs:

| | |
| --- | --- |
| pH | 7.30 |
| density[6] (g/ml) at 20° C. | 1.02252 |
| sterility | sterile |
| mean surface tension[3] (m/Nm) | |
| at 25° C. | 72.81 ± 1.86 |
| at 37° C. | 69.97 ± 0.39 |

| glass | methylacrylate | polyethylene | paraffin wax | teflon | rabbit cornea |
| --- | --- | --- | --- | --- | --- |
| contact angle at 25° C.[4]: | | | | | |
| 12.3 ± 1.9 | 60.9 ± 4.1 | 45.3 ± 5.7 | 94.3 ± 8.5 | 58.2 ± 6.0 | 40.1 ± 13.0 |
| contact angle at 37° C.[4]: | | | | | |
| 16.1 ± 3.3 | 60.2 ± 1.9 | 57.5 ± 7.0 | 95.6 ± 4.0 | 65.3 ± 7.5 | 38.8 ± 12.9 |

Notes:

[3] determined by the method of Ferguson and Kenney (1932) [Tiffany J.M., Winter N., Bliss G., "Curr. Eye Res.", 8, 507–515, 1989],

[4] determined by the procedure of Tiffany (1990) [Tiffany J.M., "Acta Ophtalmol", 68, 182–187, 1990],

[6] determined using the Ken Da-310 M Mettler-Toledo densimeter.

EXAMPLE 4

Preparation of solution E

Operating in a manner similar to that described in Example 1 above a fourth solution was prepared and comprised:

| Components | Quantity (g) |
|---|---|
| glycogen polysaccharide | 1 |
| D-mannitol | 1.8 |
| taurine | 0.3 |
| monobasic sodium phosphate $H_2O$ | 0.2 |
| dibasic sodium phosphate 12 $H_2O$ | 1.5 |
| distilled water q.s.p. | 50 ml |

The solution prepared in this way (Solution C) had the following characteristcs:

| | |
|---|---|
| pH | 7.32 |
| density[6] (g/ml) at 20° C. | 1.01602 |
| sterility | sterile |
| mean surface tension[3] (m/Nm) | |
| at 25° C. | 72.94 ± 0.61 |
| at 37° C. | 70.08 ± 0.22 |

| glass | methyl-acrylate | poly-ethylene | paraffin wax | teflon | rabbit cornea |
|---|---|---|---|---|---|
| contact angle at 25° C.[4]: | | | | | |
| 11.3 ± 2.3 | 44.3 ± 10.7 | 55.6 ± 4.3 | 78.4 ± 2.6 | 67.9 ± 4.0 | 43.4 ± 14.2 |
| contact angle at 37° C.[4]: | | | | | |
| 13.9 ± 4.0 | 51.3 ± 7.9 | 39.3 ± 5.8 | 88.7 ± 7.5 | 60.2 ± 12.9 | 19.8 ± 7.7 |

Notes:
[3]determined by the method of Ferguson and Kenney (1932) [Tiffany J.M., Winter N., Bliss G., "Curr. Eye Res.", 8, 507–515, 1989],
[4]determined by the procedure of Tiffany (1990) [Tiffany J.M., "Acta Ophtalmol", 68, 182–187, 1990],
[6]determined using the Ken Da-310 M Mettler-Toledo densimeter.

EXAMPLE 5

Preparation of Solution F

Operating in a manner similar to that described in Example 1 above a fifth solution was prepared and comprised:

| Components | Quality (g) |
|---|---|
| glycogen polysaccharide | 6 |
| D-mannitol | 1.8 |
| taurine | 0.3 |
| monobasic sodium phosphate $H_2O$ | 0.2 |
| dibasic sodium phosphate 12 $H_2O$ | 1.5 |
| distilled water q.s.p. | 50 ml |

The solution prepared in this way (Solution F) had the following characteristcs:

| | |
|---|---|
| pH | 7.38 |
| density[6] (g/ml) at 20° C. | 1.03173 |
| sterility | sterile |
| mean surface tension[3] (m/Nm) | |
| at 25° C. | 73.76 ± 0.91 |
| at 37° C. | 73.66 ± 0.74 |

| glass | methyl-acrylate | poly-ethylene | paraffin wax | teflon | rabbit cornea |
|---|---|---|---|---|---|
| contact angle at 25° C.[4]: | | | | | |
| 10.7 ± 2.1 | 60.4 ± 4.9 | 65.6 ± 6.9 | 99.9 ± 5.2 | 80.7 ± 6.7 | 98.9 ± 7.6 |
| contact angle at 37° C.[4]: | | | | | |
| 17.6 ± 3.7 | 66.8 ± 2.7 | 52.8 ± 4.1 | 95.3 ± 3.6 | 81.7 ± 11.2 | 28.8 ± 10.8 |

Notes:
[3]determined by the method of Ferguson and Kenney (1932) [Tiffany J.M., Winter N., Bliss G., "Curr. Eye Res.", 8, 507–515, 1989],
[4]determined by the procedure of Tiffany (1990) [Tiffany J.M., "Acta Ophtalmol", 68, 182–187, 1990],
[6]determined using the Ken Da-310 M Mettler-Toledo densimeter.

EXAMPLE 6

Preparation of Solution G

Operating in a manner similar to that described in Example 1 above a sixth solution was prepared and comprised:

| Components | Quantity (g) |
|---|---|
| glycogen polysaccharide | 9 |
| D-mannitol | 1.8 |
| taurine | 0.3 |
| monobasic sodium phosphate $H_2O$ | 0.2 |
| dibasic sodium phosphate 12 $H_2O$ | 1.5 |
| distilled water q.s.p. | 50 ml |

The solution prepared in this way (Solution G) had the following characteristcs:

| | |
|---|---|
| pH | 7.27 |
| density[6] (g/ml) at 20° C. | 1.04122 |
| sterility | sterile |
| mean surface tension[3] (m/Nm) | |
| at 25° C. | 74.37 ± 0.26 |
| at 37° C. | 72.63 ± 0.95 |

| glass | methyl-acrylate | poly-ethylene | paraffin wax | teflon | rabbit cornea |
|---|---|---|---|---|---|
| contact angle at 25° C.[4]: | | | | | |
| 12.8 ± 2.2 | 55.8 ± 4.1 | 54.3 ± 5.2 | 100.3 ± 3.0 | 87.3 ± 1.9 | 35.5 ± 9.9 |
| contact angle at 37° C.[4]: | | | | | |
| 15.2 ± 3.3 | 54.0 ± 3.1 | 59.8 ± 4.6 | 94.4 ± 1.5 | 76.3 ± 4.6 | 20.7 ± 4.3 |

Notes:
[3]determined by the method of Ferguson and Kenney (1932) [Tiffany J.M., Winter N., Bliss G., "Curr. Eye Res.", 8, 507–515, 1989],
[4]determined by the procedure of Tiffany (1990) [Tiffany J.M., "Acta Ophtalmol", 68, 182–187, 1990],
[6]determined using the Ken Da-310 M Mettler-Toledo densimeter.

Test 1

A double blind experiment was performed with Solution A, using the ophthalmic solution Dacriosol™ from the Alcon company (Solution D), containing dextran (0.1%) and hydroxypropylmethylcellulose (0.3%) as active ingredients, as the comparison preparation.

The experiment was performed on 11 healthy subjects of which 2 were affected by mild reddening of both eyes as a result of frequent computer use, while 1 had reddening, again of both eyes, as a result of incipient rhinitis of an allergic nature.

One drop (equal to approximately 0.05 ml) of Solution A was instilled into the left eye of each individual and one drop of Solution D into the right eye.

10–15 minutes after application the individuals were asked to describe their sensations on a card, putting a cross on a continuous 90 mm line which started from a beginning (0—total absence of feeling) to an end (maximum or marked feeling). The distance of the cross from the start expressed in millimetres constituted the score for that sensation.

The following parameters were taken into consideration:
a) sensation of wellbeing in the eyes,
b) sensation of freshness in the eyes,
c) sensation of wetness,
d) viscosity,
e) burning,
f) pain, g) lachrymation, h) sensation of the presence of a foreign body, i) blurred vision, and j) reddening of the conjunctive.

It will be noted from Tables I and II that both the solutions are well tolerated and that after an initial stage in which no individual reported any differences in sensation, after some 5–10 minutes Solution A proved to induce a greater sensation of wellbeing, freshness and wetness and a lesser sensation of viscosity and lachrymation with a consequent lesser sensation of the presence of a foreign body and blurring. This subjective assessment was confirmed in measurements of the viscosities of the two preparations (2.02 cP for Solution A and 7.6 cP for Solution D). The three individuals affected by reddening of the eyes manifested a more marked reduction in this reddening in the case of Solution A.

The above experiment was extended to a further 23 individuals. Here again the following parameters were taken into consideration:

a) sensation of wellbeing in the eyes, b) sensation of freshness in the eyes, c) sensation of wetness, d) viscosity, e) burning, f) pain, g) lachrymation, h) sensation of the presence of a foreign body, i) blurred vision, and j) reddening of the conjunctiva.

This experiment yielded results similar to Tables I and II.

TABLE I

Effects of Solution A after a single application

| No. | Eye | Wellbeing | Freshness | Wetness | Viscosity | Burning | Pain | Lachrymation | Foreign body | Blurring | Reddening | |
|---|---|---|---|---|---|---|---|---|---|---|---|---|
| 1 | L | 2.5 | 5.1 | 3.0 | 0.5 | 0 | 0 | 0 | 0 | 0 | 0 | |
| 2 | L | 1.5 | 3.9 | 3.8 | 6.2 | 0 | 0 | 0 | 0 | 0 | 0 | * |
| 3 | L | 1.0 | 3.7 | 1.0 | 0 | 0 | 0 | 0 | 0 | 0 | 0 | |
| 4 | L | 2.8 | 2.8 | 2.8 | 0.5 | 0 | 0 | 0.4 | 0 | 0 | 0 | |
| 5 | L | 0.3 | 0.3 | 0 | 0.8 | 0 | 0 | 0 | 0 | 0 | 0 | |
| 6 | L | 7.7 | 7.7 | 7.9 | 0 | 0 | 0 | 0 | 0 | 0 | 0 | |
| 7 | L | 7.3 | 7.3 | 7.2 | 0 | 0 | 0 | 0 | 0 | 0 | 0 | * |
| 8 | L | 4.0 | 4.0 | 4.0 | 0 | 0 | 0 | 0 | 0 | 0 | 0 | |
| 9 | L | 6.5 | 6.5 | 9.0 | 6.7 | 0 | 0 | 0 | 0 | 0 | 0 | ** |
| 10 | L | 6.0 | 6.1 | 5.5 | 0 | 0 | 0 | 0 | 0 | 0 | 0 | |
| 11 | L | 6.2 | 6.7 | 4.6 | 0 | 0 | 0 | 1.9 | 0 | 0 | 0 | |
| | Mean | 4.2 | 4.9 | 4.4 | 1.3 | 0.0 | 0.0 | 0.2 | 0.0 | 0.0 | 0.0 | |
| | ± | 2.68 | 2.23 | 2.83 | 2.55 | 0.00 | 0.00 | 0.57 | 0.00 | 0.00 | 0.00 | |

* Slight reduction in pre-existing reddening
** Marked reduction in pre-existing reddening

TABLE II

Effects of Solution D after a single application

| No. | Eye | Wellbeing | Freshness | Wetness | Viscosity | Burning | Pain | Lachrymation | Foreign body | Blurring | Reddening | |
|---|---|---|---|---|---|---|---|---|---|---|---|---|
| 1 | R | 2.8 | 3.7 | 5.7 | 0.4 | 0 | 0 | 1.5 | 0 | 0 | 0 | |
| 2 | R | 4.5 | 4.6 | 4.6 | 1.8 | 0 | 0 | 0 | 0 | 0 | 0 | * |
| 3 | R | 1.0 | 1.9 | 0.9 | 6.8 | 0 | 0 | 0 | 0.5 | 2.8 | 0 | |
| 4 | R | 2.8 | 2.7 | 5.2 | 6.9 | 0 | 0 | 0.5 | 0 | 3 | 0 | |
| 5 | R | 1.7 | 1.5 | 0 | 0 | 0 | 0 | 0 | 0 | 0 | 0 | |
| 6 | R | 4.8 | 8.0 | 8.0 | 0 | 1.0 | 0 | 1.1 | 0 | 0 | 0 | * |
| 7 | R | 3.0 | 2.9 | 2.9 | 7.7 | 0 | 0 | 0 | 0 | 0 | 0 | |
| 8 | R | 4.0 | 1.7 | 0.9 | 0 | 0 | 0 | 0 | 0 | 0 | 0 | * |
| 9 | R | 6.5 | 1.5 | 0.0 | 1.6 | 0 | 0 | 0 | 0 | 0 | 0 | |
| 10 | R | 6.1 | 8.1 | 7.0 | 0.7 | 0.7 | 0.7 | 1.4 | 0.9 | 0.7 | 0 | |
| 11 | R | 1.1 | 1.1 | 2.8 | 1.3 | 6.7 | 0 | 1.7 | 2.7 | 0 | 0 | |
| | Mean | 3.5 | 3.4 | 3.5 | 2.5 | 0.8 | 0.1 | 0.6 | 0.4 | 0.6 | 0.0 | |
| | ± | 1.88 | 2.51 | 2.83 | 3.07 | 2.00 | 0.21 | 0.71 | 0.83 | 1.16 | 0.00 | |

* Slight reduction in pre-existing reddening

What is claimed is:

1. A method of lubricating an eye comprising administering a composition which comprises a glycogen polysaccharide, as an active ingredient, and a opthalmically acceptable carrier, wherein said glycogen polysaccharide is substantially free of nitrogen as determined by the Kjeldahl method.

2. The method of claim 1, wherein said glycogen polysaccharide is in an amount of from 0.1 to 12% weight/volume.

3. The method of claim 2, wherein said glycogen polysaccharide is in an amount of from 1 to 6% weight/volume.

4. The method of claim 3, wherein said glycogen polysaccharide is in an amount of from 2 to 4% weight/volume.

5. The method of claim 1, wherein said composition further comprises an antioxidant.

6. The method of claim 5, wherein said antioxidant is taurine.

7. The method of claim 1, wherein said composition further comprises an agent capable of regulating isotonicity.

8. The method of claim 6, wherein said agent capable of regulating isotonicity is mannitol.

9. The method of claim 1, wherein the pH of said composition is from 5 to 8.

10. The method of claim 9, wherein the pH of said composition is from 6.5 to 7.5.

11. The method of claim 1, wherein said composition has a viscosity of from 1 to 9 cP.

12. The method of claim 2, wherein said composition has an oncotic pressure of not more than 5 mm Hg.

13. The method of claim 12, wherein said composition has an oncotic pressure of not more than 3 mm Hg.

14. A method of lubricating an eye, comprising:

administering a composition which comprises a glycogen polysaccharide, as an active agent, and an opthalmically acceptable carrier, wherein said glycogen polysaccharide is substantially free of nitrogen as determined by the Kjeldahl method and which has an oncotic pressure of not more than 5 mmHg.

* * * * *